(12) United States Patent
Bruce-Rockson

(10) Patent No.: US 11,169,134 B2
(45) Date of Patent: Nov. 9, 2021

(54) GEOLOGY MATERIAL ORGANIZER AND METHOD OF USE

(71) Applicant: Terry Kwao Bruce-Rockson, Calgary (CA)

(72) Inventor: Terry Kwao Bruce-Rockson, Calgary (CA)

( * ) Notice: Subject to any disclaimer, the term of this patent is extended or adjusted under 35 U.S.C. 154(b) by 70 days.

(21) Appl. No.: 16/671,217

(22) Filed: Nov. 1, 2019

(65) Prior Publication Data

US 2021/0132027 A1    May 6, 2021

(51) Int. Cl.
| | |
|---|---|
| *G01N 3/02* | (2006.01) |
| *G01N 3/42* | (2006.01) |
| *G01N 33/24* | (2006.01) |
| *B65D 43/16* | (2006.01) |
| *G01N 21/88* | (2006.01) |
| *G01N 17/00* | (2006.01) |
| *B65D 25/04* | (2006.01) |

(52) U.S. Cl.
CPC ............ *G01N 33/24* (2013.01); *B65D 25/04* (2013.01); *B65D 43/163* (2013.01); *G01N 3/02* (2013.01); *G01N 17/00* (2013.01); *G01N 21/8803* (2013.01)

(58) Field of Classification Search
CPC ............ G01N 29/14; G01N 3/06; G01N 3/08; G01N 29/045; G01N 29/4427; G01N 29/46; G01N 33/24; G01N 2203/0658; G01N 2291/0232; G01N 2291/0289; G01N 2291/02818; G01N 2291/02827
See application file for complete search history.

(56) References Cited

U.S. PATENT DOCUMENTS

| | | | |
|---|---|---|---|
| 2,087,043 A | 7/1937 | Phillips | |
| 3,106,788 A | 10/1963 | William | |
| 5,941,712 A | 8/1999 | Smith | |
| 6,247,358 B1 * | 6/2001 | dos Santos | ............ E21B 25/08 166/282 |
| 7,557,917 B1 | 7/2009 | Beesley | |
| 9,797,868 B2 * | 10/2017 | Macleod | ............ G01N 29/045 |
| 10,119,901 B2 | 11/2018 | Casas | |
| 2008/0311605 A1 | 12/2008 | Klein et al. | |

FOREIGN PATENT DOCUMENTS

| | | |
|---|---|---|
| CN | 105551360 A | 5/2016 |
| CN | 207432170 U | 6/2018 |
| KR | 101253521 B1 | 4/2013 |
| KR | 101399910 B1 | 5/2014 |

* cited by examiner

*Primary Examiner* — Brandi N Hopkins
(74) *Attorney, Agent, or Firm* — Orin Del Vecchio

(57) ABSTRACT

A geology materials organizer configured to receive and retain a plurality of elements configured to provide a method of testing a rock or mineral sample. The geology materials organizer of the present invention includes a case wherein the case has an interior volume having implements releasably secured therein. A plurality of mohs hardness picks are releasably secured within the case. The geology materials organizer further includes providing a streak plate and an acid dispenser that are operable to assist in performing additional test on rocks or mineral samples. The case of the present invention further includes a lid and a transparent map pocket. Disposed within the interior volume of the case are a plurality of mineral receptacles configured to receive an retain mineral samples. The geology materials organizer further includes an ultraviolet light and a magnet.

14 Claims, 2 Drawing Sheets

GEOLOGY MATERIAL ORGANIZER AND METHOD OF USE

FIELD OF THE INVENTION

The present invention relates generally to organizational devices, more specifically but not by way of limitation, a geology tool organizational device that is configured to supply and organize the necessary tools so as to execute mineralogical study of rocks and/or samples thereof.

BACKGROUND

As is recognized in the art the study of rocks and minerals is known as geology. Geology studies and techniques thereof are utilized in various industries and academic fields. Industries such as but not limited to the oil and gas industry will study rocks, mineral contents and soil layers so as to potentially identify areas that may have hydrocarbon content indicating the potential presence of oil or other energy substances such as natural gas. In the academia field, geology studies can be used in subfields of archaeology or in the primary field of geology itself. In the field of geology, the study of rocks and minerals are executed to determine parameters such as but not limited to age of rocks and the composition thereof. In order to execute the aforementioned, many tools and/or implements are utilized. These tools can include but are not limited to magnets, streak plates, acid and acid droppers and ultra-violet light sources.

One issue with current execution of geological studies is the lack of integrated organizers and supplies for implements and tools that are required to perform various geological studies. Most individuals who are engaged in geological studies must separately purchase and maintain the various tools/implements needed to perform the various tests. The purchasing of the tools/implements separately can be cost prohibitive. Additionally, for those individuals such as but not limited to students, the lack of a consolidated resource that supplies all of the required materials and tools to execute geological studies is both inconvenient and can lead to a student not having all of the tools necessary to perform the required studies.

Accordingly, there is a need for a geology material organizer that provides a consolidated source and method for executing geological studies on rocks and minerals.

SUMMARY OF THE INVENTION

It is the object of the present invention to provide a geology material organizer that provides a consolidated resource for tools and implements required to execute geological studies wherein the present invention includes a case that is configured to receive and maintain tools and other implements operable to perform geological tests.

Another object of the present invention is to provide a geology material organizer and method that provides tools and a procedure for executing geological studies wherein the case of the present invention includes a plurality of compartments and receptacles for receiving tools and/or materials therein.

A further object of the present invention is to provide a geology material organizer that provides a consolidated resource for tools and implements required to execute geological studies wherein the case of the present invention further includes a transparent grain sizing chart.

Still another object of the present invention is to provide a geology material organizer and method that provides tools and a procedure for executing geological studies wherein the case of the present invention further includes at least one geological map holder.

An additional object of the present invention is to provide a geology material organizer that provides a consolidated resource for tools and implements required to execute geological studies wherein the present invention includes implements such as but not limited to streak plates, magnifying lens and a ultra-violet light source.

Yet a further object of the present invention is to provide a geology material organizer and method that provides tools and a procedure for executing geological studies wherein the present invention further includes a plurality of mineral samples stored in internal compartments within the interior volume of the case.

Another object of the present invention is to provide a geology material organizer that provides a consolidated resource for tools and implements required to execute geological studies that further includes a plurality of implements operable to identify mohs hardness of a rock sample.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
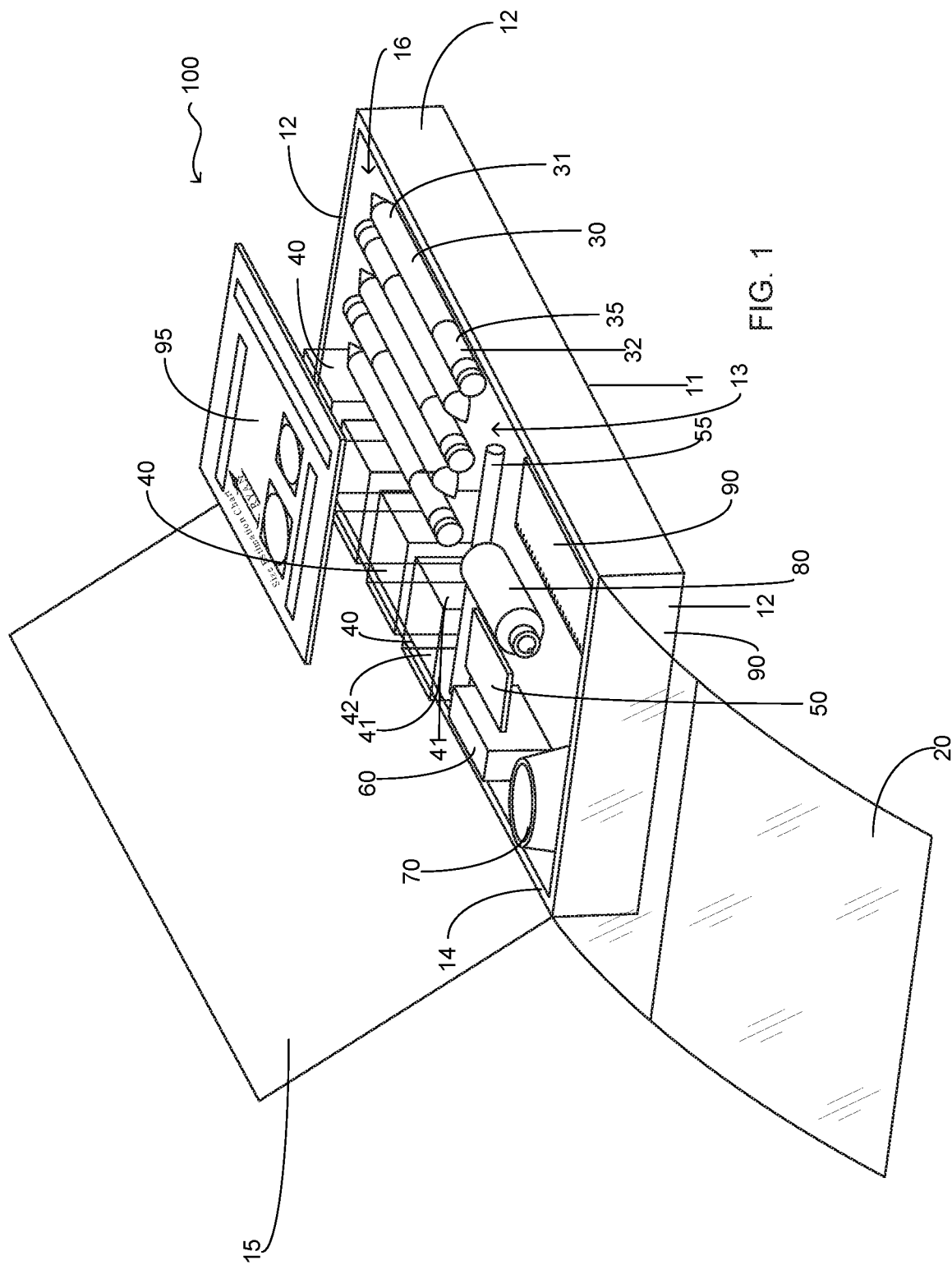
FIG. 1 is a perspective view of the present invention.

Referring now to the drawings submitted herewith, wherein various elements depicted therein are not necessarily drawn to scale and wherein through the views and figures like elements are referenced with identical reference numerals, there is illustrated a geology materials organizer 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to FIG. 1, the geology materials organizer 100 includes a case 10 wherein the case 10 is manufactured from a suitable durable material such as but not limited to plastic. The case 10 includes a bottom 11 and a plurality of walls 12 integrally formed to create an interior volume 13. It should be understood within the scope of the present invention that the case 10 could be manufactured in alternate sizes and shapes. The rear wall 14 has a lid 15 hingedly secured thereto. Lid 15 functions to move between an open and closed position so as to either cover the opening 16 or provide access thereto facilitating access to the interior volume 13.

The case 10 further includes map pocket 20. Map pocket 20 is designed to releasably secure articles such as but not limited to maps. The map pocket 20 is hingedly secured to side wall 19 utilizing suitable durable techniques. In a preferred embodiment, the map pocket 20 is manufactured from a transparent material so as to allow visibility of materials while secured therein. It is contemplated within the scope of the present invention that the map pocket 20 could be dual-sided so as to retain more than one map.

The geology materials organizer 100 includes a plurality of elements disposed within the interior volume 13 thereof. The elements are configured to facilitate a user thereof perform various tests and analysis that are required during conventional geological studies. The geology materials organizer 100 includes a plurality of mohs hardness picks 30. As is known in the art, mohs hardness is a scale that is used to identify the hardness of the rock or mineral. The mohs hardness picks 30 include a first end 31 and a second end 32. The first end 31 and second end 32 are configured to identify a mohs hardness scale that are adjacent to each other. By way of example but not limitation, the mohs hardness pick 30 could be configured to test for a three and a four wherein the first end 31 is configured to test for a mohs hardness of three and the second end 32 is configured to test for a mohs hardness of four. Releasably secured to second end 32 is cap 35. The cap 35 is frictionally engaged with the mohs hardness picks 30 and is configured to provide protection of the second end 32. In a preferred embodiment, the geology materials organizer 100 includes five mohs hardness picks 30 that are configured to provide testing of rocks and/or minerals from a range of one to ten on the mohs hardness scale. The mohs hardness picks 30 are releasably secured within the interior volume 13 of the case 10 utilizing suitable durable techniques. BY way of example but not limitation, the mohs hardness picks 30 could be releasably secured utilizing magnets and/or clips.

The interior volume 13 of the case 10 further includes a plurality of mineral receptacles 40. The mineral receptacles 40 are secured within the interior volume 13 utilizing suitable durable techniques. The mineral receptacles 40 are constructed utilizing a plurality of walls 41 and top 42 in order to create an interior volume suitable for receiving and retaining mineral samples therein. While the mineral receptacles 40 are illustrated herein as being rectangular in shape, it is contemplated within the scope of the present invention that the mineral receptacles 40 could be formed in alternate shapes and sizes and still achieve the desired functionality as described herein. Additionally, it should be understood within the scope of the present invention that the geology materials organizer 100 could have as few as one mineral receptacle 40 or a plurality of mineral receptacles 40.

The geology materials organizer 100 further includes a streak plate 50. As is known in the art, a mineral streak plate is an unglazed porcelain plate used to test the characteristic streak of minerals up to a hardness of six and a half mohs. The streak plate 50 is provided in a rectangular shape and is releasably secured within the interior volume 13 of the case 10 utilizing suitable durable techniques. While one streak plate 50 is illustrated herein, it is contemplated within the scope of the present invention that the geology materials organizer 100 could be provided with more than one streak plate 50. Adjacent to the streak plate 50 is the UV pen light 55. The UV pen light 55 is a battery powered pen light that is operable to emit ultra-violet light therefrom. Ultraviolet light is utilized to test rock characteristics and whether or not the rock will glow once exposed to ultraviolet light. The UV pen light 55 is secured utilizing suitable techniques within the interior volume 13 of the case 10.

Further included within the geology materials organizer 100 is a magnet 60. The magnet 60 is a conventional magnet and is utilized in the geological field to determine if a mineral or rock being studied is magnetic. While the magnet 60 is illustrated herein as being rectangular, it should be understood within the scope of the present invention that the magnet 60 could be provided in alternate sizes and shapes. Adjacent to the magnet 60 is the magnifying lens 70. The magnifying lens 70 is a conventional magnifying lens and is releasably secured within the geology materials organizer 100. As is known in the art magnifying lenses are utilized to examine the surface characteristics of rocks and/or minerals. While no particular magnifying power is required, in the preferred embodiment of the present invention the magnifying lens 70 is 10×.

Adjacent to the streak plate 50 is acid container 80. Acid container 80 is releasably secured within the interior volume 13 of the case 10 utilizing suitable durable techniques. The acid container 80 is configured to receive, retain and dispense an acid such as but not limited to hydrochloric acid. As is known in the art, hydrochloric acid is placed on a mineral or rock and the mineral/rock is observed for the presence of bubbles. The bubbles are a release of carbon dioxide gas, which indicates the presence of carbonate materials. It is contemplated within the scope of the present invention that the acid container 80 could be provided in alternate shapes and sizes.

Disposed within the geology materials organizer 100 are a plurality of charts 90,95. The charts 90,95 are provided with information thereon that is configured to assist in the study of rocks and/or minerals. In the preferred embodiment at least one of the charts 90,95 is manufactured from a transparent material. The charts 90,95 include at least one having the information and/or material imprinted thereon that is operable to determine grain size of a rock and/or mineral. It is further contemplated within the scope of the present invention that the charts 90,95 could be provided with information imprinted thereon such as but not limited to rock classification, streak plate colors and mohs hardness scale. While two charts 90,95 are illustrated herein, it should be understood within the scope of the present invention that as few as one chart could be provided or more than two charts.

Figure 2:
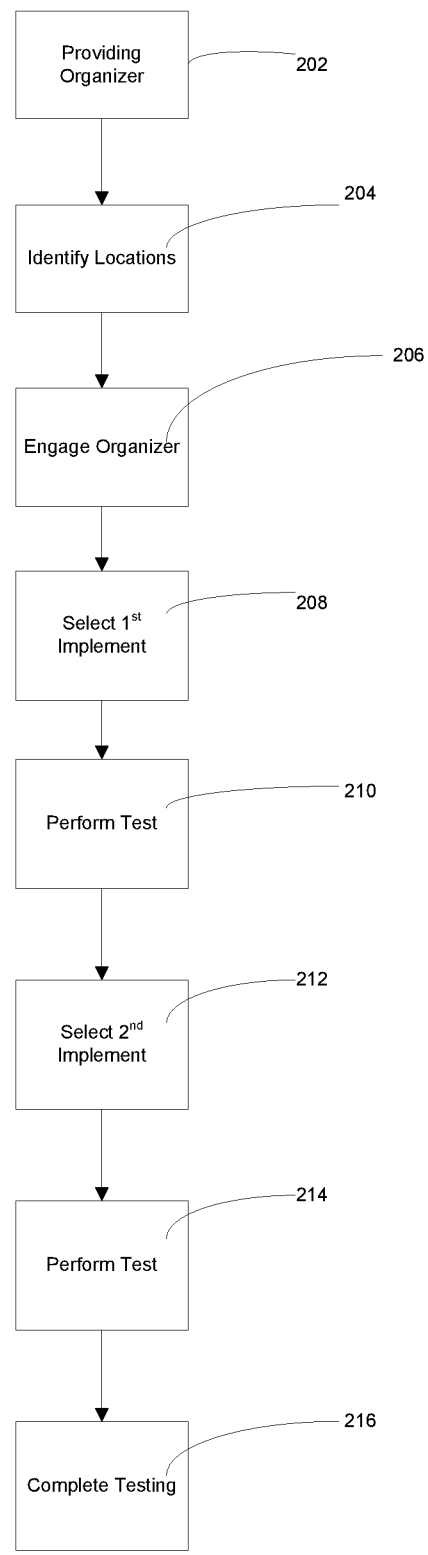
FIG. 2 is a flow chart of the method of the present invention.

Referring in particular to FIG. 2, the method of the present invention is illustrated therein. In use, the method for geology materials organizer 100 includes step 202 wherein the step includes providing a geology materials organizer 100 to a user. In step 204, the user will identify a location wherein the location will have rocks and or minerals that the user desired to study and/or identify. Step 206 comprises engaging the geology materials organizer 100 wherein the lid 15 is moved to its open position. In step 208, a user will select a first implement from the plurality of implements that are provided in the interior volume 13 of the case of the geology materials organizer 100. Step 210 comprises utilizing the selected implement, such as but not limited to one of the mohs hardness picks 30, and performing the test facilitated by the selected implement. In step 212, a user will select a second implement disposed within the interior volume 13 of the case 10 of the geology materials organizer 100. Step 214 includes performing the test facilitated by the implement selected in step 212. In step 216, a user will complete the desired testing on a rock or mineral sample utilizing the implement selected in step 212 or through alternate selection of implements until the desired types and/or quantity of tests are executed.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A method of executing a test on at least one rock or mineral sample utilizing a geology materials organizer, the method comprising the steps of:
   providing the geology materials organizer, said geology materials organizer having a case wherein the case includes a plurality of walls and a bottom forming an interior volume, said case further having an opening providing access to said interior volume, said case further including a lid, said lid being hingedly secured to one of said plurality of walls, said case being operable to receive and retain a plurality of rock or mineral testing implements;
   identifying a location, said identifying a location where the at least one rock or mineral sample can be found;
   engaging the geology materials organizer, wherein a user will access the interior volume of the case so as to identify an implement for performing a desired test;
   performing a first test, wherein a user will utilize the identified first implement to perform a test on a rock or mineral sample;
   recording a result from the test, wherein the user will record the results from the test utilizing suitable techniques; and
   wherein the geology materials organizer is configured to retain additional informational documents for use during geological studies.

2. The method of executing a test on at least one rock or mineral as recited in claim 1, wherein the step of identifying a location uses a map and the case further includes a map pocket, said map pocket being movably secured to one of said plurality of walls of said case, said map pocket configured to receive and retain the map.

3. The method of executing a test on at least one rock or mineral as recited in claim 2, and further including the step of selecting a second implement, wherein the second implement is configured to perform a different test than said first implement.

4. The method of executing a test on at least one rock or mineral as recited in claim 3, and further including the step of performing a second test, wherein the second test is executed utilizing the second implement.

5. The method of executing a test on at least one rock or mineral as recited in claim 4, wherein the test is a hardness test based a range of mohs hardness between one and ten and wherein said case further has disposed therein a plurality of mohs hardness picks, wherein the mohs hardness picks are configured to test a rock or mineral sample within a range of mohs hardness between one and ten.

6. The method of executing a test on at least one rock or mineral as recited in claim 5, wherein the test is a streak test performed on a streak plate and wherein the geology materials organizer further includes at least one streak plate, said at least one streak plate being releasably secured within the interior volume of the case.

7. The method of executing a test on at least one rock or mineral as recited in claim 6, wherein the test is an acid test for carbonate detection and wherein the case further includes an acid dispenser, said acid dispenser being releasably secured within said interior volume of said case, said acid dispenser operable to retain and dispense acid onto a rock sample for determination of a presence of carbonate.

8. A method of executing a plurality of tests on at least one rock or mineral sample utilizing a geology materials organizer, the method comprising the steps of:
   providing the geology materials organizer, said geology materials organizer having a case wherein the case includes a plurality of walls and a bottom forming an interior volume, said case further having an opening providing access to said interior volume, said case further including a lid, said lid being hingedly secured to one of said plurality of walls;
   providing a plurality of mohs hardness picks, said mohs hardness picks being releasably secured within the interior volume of the case, said mohs hardness picks operable to test a mohs hardness between one and ten;
   offering a map pocket, said map pocket being hingedly secured to one of said plurality of walls of said case, said map pocket being manufactured from a transparent material, said map pocket configured to receive and retain two geological maps;
   identifying a location, said identifying a location where at least one rock or mineral sample can be found;

engaging the geology materials organizer, wherein a user will access the interior volume of the case so as to identify an implement for performing a desired test;

performing a test, wherein a user will utilize the identified implement to perform a test on a rock or mineral sample;

recording a result from the test, wherein the user will record the results from the test utilizing suitable techniques; and completing a series of test, wherein the user will utilize the implements disposed within the interior volume of the case of the geology materials organizer to perform a desired plurality of tests on a rock or mineral sample.

9. The method of executing a test on at least one rock or mineral as recited in claim 8, wherein the test is a streak test performed on a streak plate and wherein the geology materials organizer further includes at least one streak plate, said at least one streak plate being releasably secured within the interior volume of the case and said at least one streak plate is configured to test streak characteristics of a rock or mineral sample.

10. The method of executing a test on at least one rock or mineral as recited in claim 9, and further including the step of providing an acid dispenser, said acid dispenser being releasably secured within said interior volume of said case, said acid dispenser operable to retain and dispense acid onto a rock sample for determination of a presence of carbonate.

11. The method of executing a test on at least one rock or mineral as recited in claim 10, and further including the step of providing a magnifying lens, said magnifying lens being releasably secured within said interior volume of said case, said magnifying lens configured to examine a surface of the rock or mineral sample.

12. The method of executing a test on at least one rock or mineral as recited in claim 11, further including the step of providing a magnet, said magnet being releasably secured within said interior volume of said case, said magnet configured to determine magnetic characteristics of the rock or mineral sample.

13. The method of executing a test on at least one rock or mineral as recited in claim 12, and further including the step of providing a plurality of mineral receptacles, said plurality of mineral receptacles being disposed within said interior volume of the case, said mineral receptacles configured to receive and store therein a mineral sample.

14. The method of executing a test on at least one rock or mineral as recited in claim 13, and further including an informational chart, said informational chart configured to be superposed the implements disposed within the interior volume of the case of the geology materials organizer.

* * * * *